United States Patent
Jenkins, Jr.

(10) Patent No.: US 7,967,015 B2
(45) Date of Patent: Jun. 28, 2011

(54) HIGH RESILIENCE FLANGED EARPLUG

(75) Inventor: John Allen Jenkins, Jr., San Diego, CA (US)

(73) Assignee: Sperian Hearing Protection, LLC, San Diego, CA (US)

( * ) Notice: Subject to any disclaimer, the term of this patent is extended or adjusted under 35 U.S.C. 154(b) by 102 days.

(21) Appl. No.: 11/709,544

(22) Filed: Feb. 22, 2007

(65) Prior Publication Data

US 2007/0221232 A1   Sep. 27, 2007

Related U.S. Application Data

(60) Provisional application No. 60/784,341, filed on Mar. 21, 2006.

(51) Int. Cl.
*A61F 11/00* (2006.01)
(52) U.S. Cl. ........................................ 128/864; 128/857
(58) Field of Classification Search .................... 128/864
See application file for complete search history.

(56) References Cited

U.S. PATENT DOCUMENTS

| 4,867,149 | A | | 9/1989 | Falco | |
|---|---|---|---|---|---|
| 5,188,123 | A | * | 2/1993 | Gardner, Jr. | 128/864 |
| 5,727,566 | A | * | 3/1998 | Leight | 128/857 |
| 6,006,857 | A | * | 12/1999 | Leight et al. | 181/135 |
| 6,129,175 | A | * | 10/2000 | Tutor et al. | 181/135 |
| 6,241,041 | B1 | * | 6/2001 | Leight | 181/135 |
| 6,286,622 | B1 | * | 9/2001 | Tiemann | 181/135 |
| 7,107,993 | B2 | * | 9/2006 | Magidson | 128/864 |
| 7,210,484 | B1 | * | 5/2007 | Tiemens et al. | 128/864 |
| 2003/0172938 | A1 | * | 9/2003 | Falco | 128/864 |
| 2004/0045558 | A1 | * | 3/2004 | Taylor et al. | 128/864 |
| 2004/0163653 | A1 | * | 8/2004 | Fleming | 128/864 |
| 2007/0000499 | A1 | * | 1/2007 | Buck et al. | 128/864 |

FOREIGN PATENT DOCUMENTS

WO   WO 98/31313   7/1998

\* cited by examiner

*Primary Examiner* — Patricia M Bianco
*Assistant Examiner* — Victoria Hicks
(74) *Attorney, Agent, or Firm* — Leon D. Rosen

(57) ABSTRACT

An earplug has a single very long main flange with a maximum diameter that is at least 80% of the length of the main flange, and at least 55% of the entire length of the earplug except for the stem. This allows the outside of the long flange to extend at a very small angle to the axial direction, and apply a constant force against the walls of the ear canal, for good and comfortable sealing to the ear canal.

9 Claims, 3 Drawing Sheets

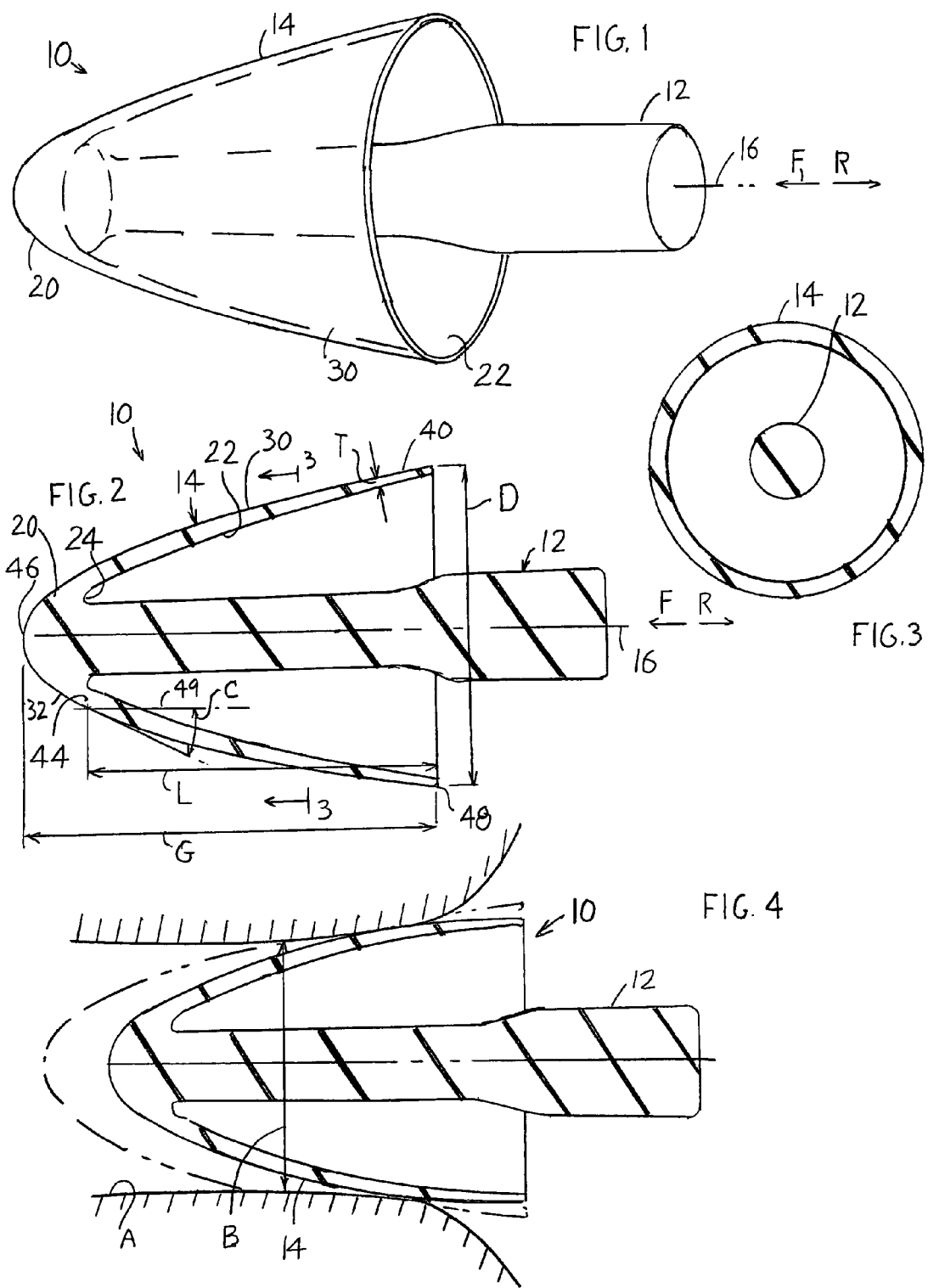

HIGH RESILIENCE FLANGED EARPLUG

CROSS-REFERENCE

Applicant claims priority from U.S. Provisional patent application Ser. No. 60/784,341 filed Mar. 21, 2006.

BACKGROUND OF THE INVENTION

Two major types of earplugs are foam earplugs and flange earplugs. Flange earplugs are usually molded of nonfoam elastomeric material and rely on the radially inward deflection of thin flanges to seal to the walls of the ear canal. Two widely sold flange earplugs are described in U.S. Pat. Nos. 4,867,149 and 6,241,041. These earplugs each have a stem and three tapered flanges that each can be inwardly deflected by the walls of a person's ear canal. The three flanges include a rearward flange of greatest diameter at its rear end, a front flange of smallest diameter at its rear end, and a middle flange of an in between diameter at its rear end. The three flanges are provided to seal well to ear canals of different diameters. Most ear canals vary in diameter between about 0.33 inch (8.4 mm) and 0.27 inch (6.86 mm), with some ear canals being of elliptical cross-section instead of circular, and with the axis of many ear canals curving.

It is recognized in U.S. Pat. No. 7,305,992 that it is desirable that the rear parts of flanges that will engage the ear canal, extend at small angles to the surfaces of the ear canal. That patent application achieves this by extending front parts of the flanges primarily radially, to locate the rear parts near the ear canal surface. However, the flanges are not as resilient as would be desired. An earplug of the flange type, that assured low pressure, wide area, contact of a flange with the ear canal walls for ear canals of a variety of sizes, would be of value.

SUMMARY OF THE INVENTION

In accordance with one embodiment of the present invention, a flanged earplug is provided that is integrally molded of resilient material, and which assures low pressure, wide area flange contact with the surface of an ear canal for ear canals of a variety of sizes. The earplug has a front end part, a stem that extends rearward along the earplug axis from the front end part, and a main flange that extends at a rearward and radially outward incline from the front end part. The main flange rear end has a flange outside diameter of about 0.50 inch (12.7 mm), which is typical for a prior art earplug flange. However, the main flange has a length that is at least 80% of the length of the main flange and at least 55% of the length of the earplug other than the stem. This very long length results in the main flange having high resilience, with its rear end extending almost parallel to the axis, so the rear end is easily deflected radially inward by an ear canal. Because of the long length of the main flange, both its front portion and its rear portion can extend primarily parallel to the axis.

An internal flange can be provided that lies within the main flange and that bears against the inside surface of the main flange to bias it radially outward. A backup flange can be provided that lies in front of the main flange and that is of short axial length. The backup flange can seal to a small diameter ear canal even if the main flange is only partially inserted into the ear canal, or if the main flange does not provide a sound seal for some other reason.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of an earplug of one embodiment of the invention.

FIG. 2 is a sectional side view of the earplug of FIG. 1.

FIG. 3 is a sectional view taken on line 3-3 of FIG. 2.

FIG. 4 is a sectional view of the earplug of FIG. 2 during insertion of the earplug into a person's ear canal, and showing, in phantom lines, the ear plug inserted slightly further into the ear canal.

DESCRIPTION OF THE PREFERRED EMBODIMENTS

Figure 5:
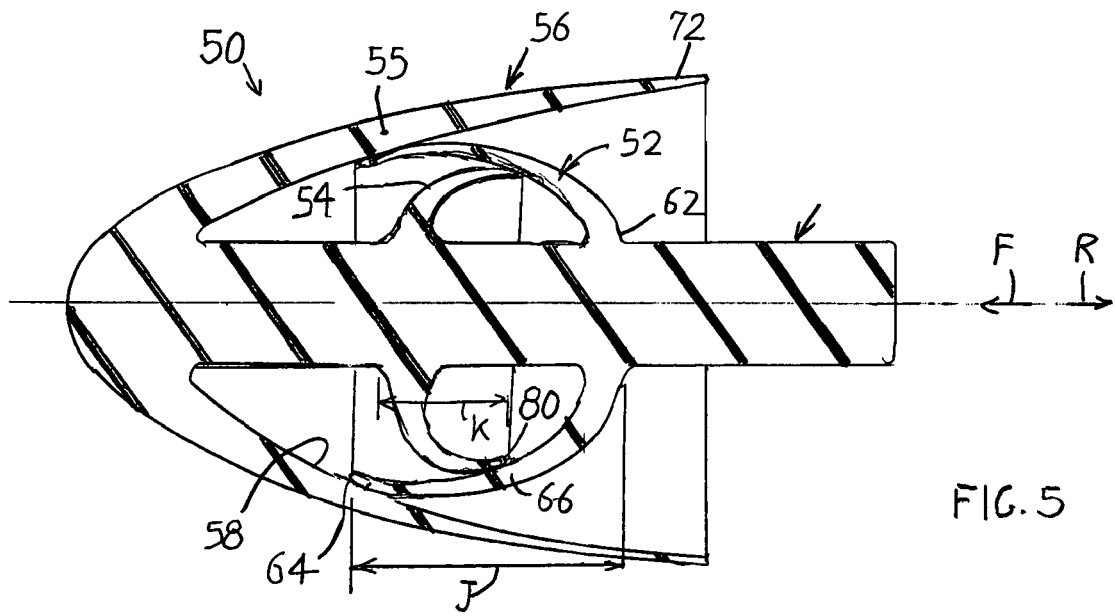
FIG. 5 is a sectional view of an earplug of another embodiment of the invention, wherein the earplug includes internal flanges that lie within the main flange.

FIGS. 1 and 2 illustrate an earplug 10 of the invention which is of simple construction and which seals well to ear canals of different diameters. The earplug includes a stem 12 and a main flange 14 that each extends rearward R along an axis 16 of the earplug from a front end part 20 of the earplug. The main flange has a progressively greater diameter at progressively more rearward locations. The main flange has an inside surface 22 that joins to the stem at a location 24, and the main flange has an outside surface 30 that merges with the front end part to form a smooth convexly curved earplug front end outside surface 32. The earplug is symmetric about the axis 16. The main flange 14 is spaced outward of the stem 12 along the entire length L of the main flange that lies rearward of the main flange front end 44. It can be seen from FIG. 4 that the earplug is devoid of any forward portion that lies forward of the flange front end 44, that is of sufficient diameter to block the ear canal A.

The ear canal A shown in FIG. 4 has an entrance with a diameter B such as 0.30 inch. Most people have ear canals with an entrance diameter of between about 0.33 inch (8.4 mm) and 0.27 inch (6.86 mm). There is also variation in the cross-sectional shape of the ear canal (slightly elliptical instead of round) and the axes of many ear canals are curved. The rear end 48 of the main flange 14 of FIG. 2 is a free end and has an initial diameter D of about 0.48 inch (12.2 mm) and is expected to be radially compressed (with respect to axis 16) to press firmly against the internal surface of the ear canal. It can be seen from FIG. 4 that the earplug is devoid of a forward portion lying forward of the flange 14, that is of sufficient diameter to block the ear canal. The earplug is molded of an elastomeric material such as silicone having a durometer A of about 30. The stem 12 and main flange 14 are integrally molded. It is desirable that the total expansion force of the flange against the walls of the ear canal be about two ounces. This assures sufficient radially inward deflection of the flange rear portion 40 so the flange presses firmly against the ear canal at all locations around the flange to prevent the passage of sound around the flange. This also avoids large forces that can bring discomfort to the wearer. The flange 14 is of progressively greater diameter from its front end (44) to its rear end 48.

The single long flange 14 has high resilience because of its length. As a result, the flange rear portion 40 applies a primarily constant force against the ear canal despite the flange bearing against walls of a small ear canal (e.g. diameter B of 0.27 inch) or a large ear canal (e.g. diameter B of 0.33 inch). It is desirable that the flange bear with about the same force (e.g. 2 ounces, or 54 grams) against small and large diameter ear canal walls. If the flange had a smaller length L, such as about half its maximum undeflected diameter D, then the force of the flange rear portion against the ear canal walls would vary more with variation of the ear canal diameter.

Prior earplug flanges, such as those shown in U.S. Pat. Nos. 4,867,149 and 6,241,041 had flange lengths no more than 62% of their largest diameters, resulting is less resilience and therefore a greater change in force with ear canal diameter. Applicant prefers to use a main flange length L that is at least 80%, of the undeflected main flange largest diameter D, that is preferably at least 90% of the diameter D, and that is more preferably at least 100% of the diameter D.

The flange 14 has a thickness T that varies along its length. The thickness is greatest at the front end 44 of the flange and gradually decreases towards the rear of the flange. The thinner flange rear portion allows better conforming of the flange rear portion to irregularities in the ear canal walls, while the thicker flange front portion provides greater resistance to deflection that balances the smaller force of the thin flange front portion. It is desirable that there be substantial radially inward deflection of the rear of the flange, to assure that it presses firmly against the surface of the ear canal.

The stem 12 is used to insert the earplug into the ear and to withdraw it. The stem usually extends rearward of the main flange, and its diameter does not have much effect on the earplug. Applicant has constructed earplugs of the construction shown in FIGS. 1-4. The earplugs had a main flange outside diameter D of 0.48 inch and a main flange length L of 0.53 inch, for a diameter-to-length ratio of 110%. The entire length G of the earplug front portion 45 (which does not include the stem) between the extreme front end 46 of the front end part and the rear end 48 of the main flange was 0.63 inch. The diameter D of the earplug rearmost flange, which is the main flange 14, is at least 55%, preferably at least 65% and most preferably at least 75% of the entire length G of the earplug front portion, that is, up to the rear end 48 of the main flange (which is the flange of greatest length). The angle C between the main flange outside surface and a line 49 that is parallel to the axis 16, varies from about 25° at the flange front end 44 to about 5° at the flange rear end 48. The main flange inner and outer surfaces (22, 30) each extends at rearward and outward incline from the stem front location along a majority of the main flange length. The main flange rear end diameter should be between 0.35 inch and 0.60 inch, and the main flange axial length should be at least 0.45 inch.

FIGS. 5 though 7 illustrate an earplug 50 that is similar to that of FIG. 1, except that it includes internal flanges 52, 54 that radially-outwardly bias a location 55 (a ring-shaped location) on the main flange 56. The rearward internal flange 52 has a rear end 62 that merges with the stem, a front end 64 that bears against the inside 58 of the main flange, and a middle portion 66. The rearward internal flange 52 biases the middle 55 of the main flange radially outward. This results in the main flange rear portion 72 pressing more firmly against the ear canal without requiring a thicker flange, so a thin main flange can be used that conforms to local irregularities in the ear canal. The rearward internal flange has a considerable length J and thin walls especially at its front end 64 so it is highly resilient.

The forward internal flange 54 is thin and of length K. Its rear end 80 urges the middle of the rearward internal flange radially outwardly. The combination of the main flange with one or both of the internal flanges, results in resilient outwardly biasing of the main flange.

Figure 6:
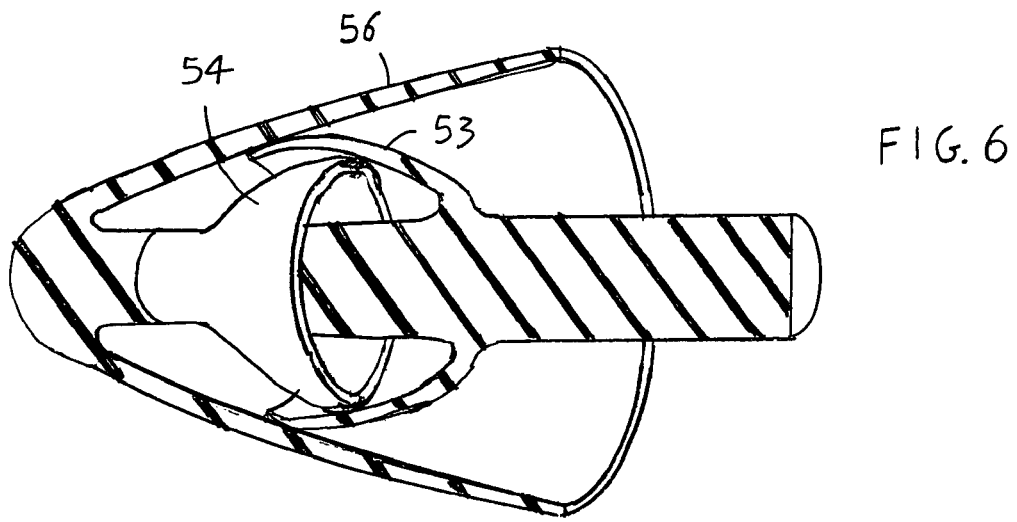
FIG. 6 is a sectional isometric view of the earplug of FIG. 5.
Figure 7:
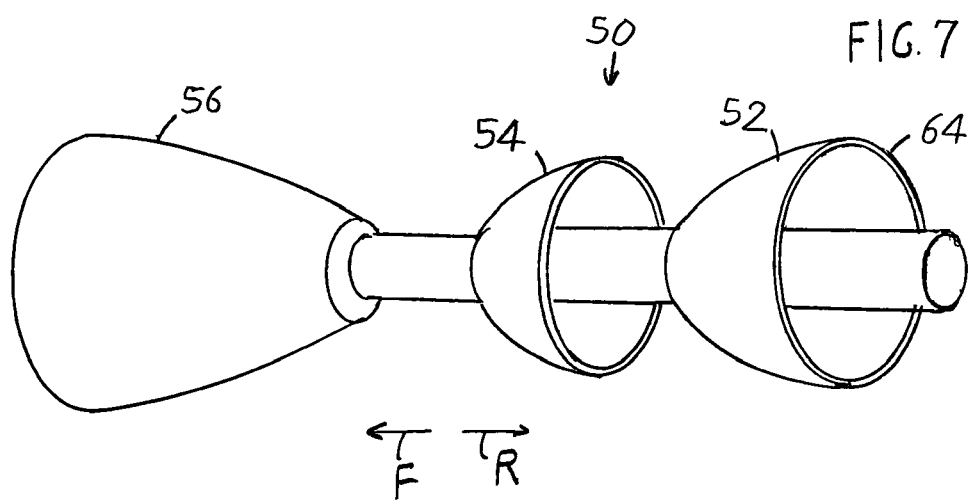
FIG. 7 is an isometric view showing the earplug of FIG. 6 after it is molded but before two of the flanges are reversed to achieve the final configuration of FIG. 6.

FIG. 7 shows how the one-piece molded earplug 50 of FIGS. 5 and 6 can be molded, with the main flange 56 initially opening forwardly and the two umbrella-shaped internal flanges 52, 54 opening rearwardly. After molding, the rear end portion 64 of the rear internal flange 52 is deflected to "snap" it in reverse so it opens forwardly as in FIG. 5. Then the main flange 56 is "snapped" in reverse so it opens rearwardly as in FIG. 5.

Although the earplugs with the long main flange 14 of FIG. 1 and the long main flange 56 of FIG. 5 can provide good sound sealing, they lack a "backup", or second location where the earplug seals to the walls of the ear canal. Such a backup location has an advantage in providing a sound seal in the event that there is an irregularity in the ear canal, such as a small bump where the main flange rear portion presses against the ear canal and where an air gap might be left, or where the earplug is inserted only a small part of the total designed insertion distance into the ear canal.

Figure 8:
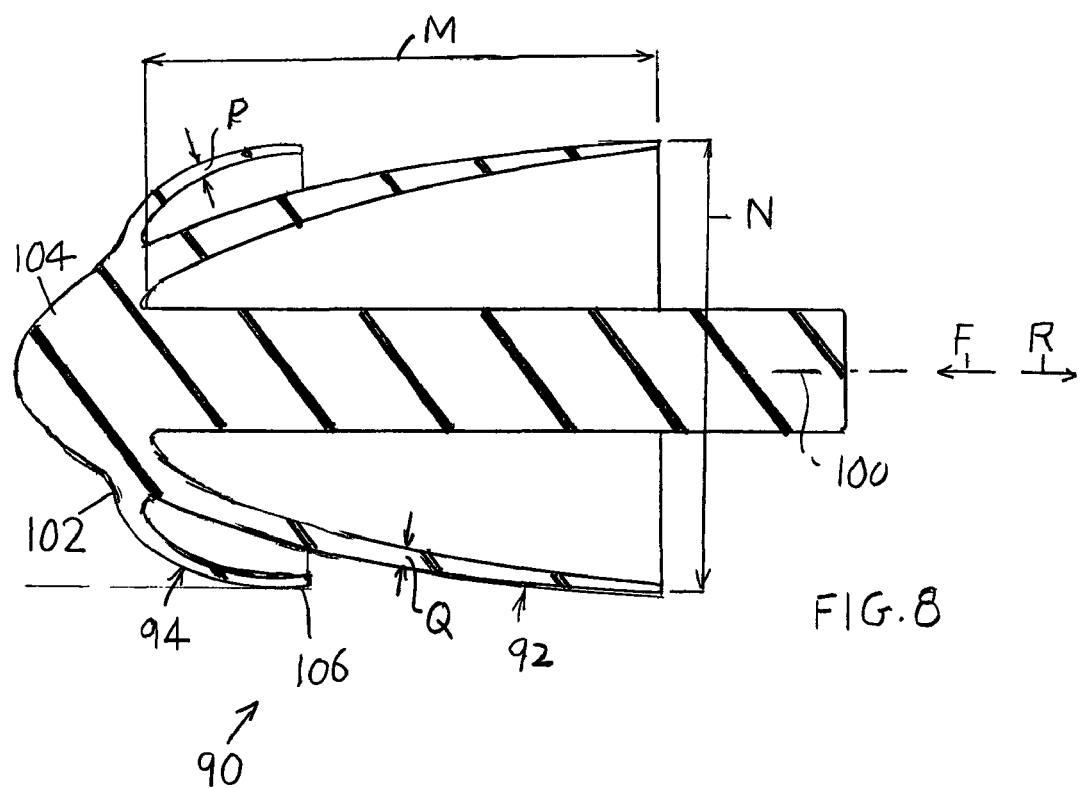
FIG. 8 is a sectional side view of an earplug of another embodiment of the invention wherein the earplug includes a short backup flange that lies forward of the main flange.

FIG. 8 illustrates an earplug 90 that includes a main flange 92 and a backup flange 94 that "piggybacks" on the main flange. The main flange 92 is similar to those of the prior two embodiments of the invention, with a length M along the earplug axis 100 that is over at least 75%, preferably at least 90%, and more preferably at least 100% of the main flange maximum outside diameter N. The backup flange 94 has a front end 102 that lies slight forward of the main flange and merges with an earplug front part 104. The backup flange has a rear end 106 that has about the same diameter as the rear of the main flange. However, the backup flange has an average thickness P that is about half the average thickness Q of the main flange and slightly more sound can penetrate the backup flange. In most cases, the main flange seals well against the ear canal walls and the backup flange seals also, though not quite as well. However, when the main flange does not seal well, the moderately good sealing of the backup flange protects the hearing of the worker from damage.

Applicant prefers to mold the earplug of a "solid" (not foam) elastomeric material such as silicone. However, it is possible to mold the earplug of a foam material, preferably one of a high density foam. In either case, the earplug is a one-piece molded article.

Thus, the invention provides an earplug of a type that has a stem and that has a flange that extends at a rearward and radially outward (with respect to the axis) incline as seen in a sectional view, wherein the flange has an especially high resilience so it can provide a force on the order of magnitude of two ounces against the ear canal despite variation in the diameter of the ear canal. This is accomplished by using a main flange that extends along most of the length of the earplug other than the stem, with the main flange length being at least 80% (more than 75%), 90% or 100% of the largest diameter of the main flange. The resilience of the main flange can be enhanced by providing an internal flange that extends from the stem, preferably at an average incline of no more than 30° to the axis, and that presses against the inside surface of the main flange to resiliently bias it radially outward. A second internal flange can bias the first internal flange outward. The earplug can be provided with a backup flange that has about the same or slightly smaller rear portion diameter but a smaller length and thickness than the main flange. Such backup flange assures a moderate sound seal in the event that the main flange does not provide a good sound seal.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug of elastomeric material having an axis (16) extending in front and rear directions, said earplug having a front end part (20), a stem (12) extending rearward from said front end part, a main flange (14) having an inside forming an inner surface (22) and an outside forming an outer surface (30) with each surface extending at a rearward and radially outward incline from a stem front location, and with said inner surface spaced outward from said stem at all main flange locations that lie rearward of a front end (44) of the main flange, said inner surface lying closer to said axis than said outer surface, wherein:
said stem and said main flange are integrally molded so they are formed of the same material, and said flange has a free rear end (48);
said main flange has an outside diameter that is fitable into a human ear canal to block it with the flange rear end being radially inwardly deflected, and the flange has a length (L) along said axis along which said flange outer surface extends at a rearward and outward incline away from the axis that is at least 80% of the maximum outside diameter (D) of said main flange, and said main flange inner and outer surfaces each extends at a rearward and outward incline along a majority of the main flange length, with said outer surface (30) extending at an angle (C) with respect to said axis (16) along a majority of the main flange length (L), where said angle (C) is between 5° and 25°.

2. The earplug described in claim 1 wherein:
said earplug includes at least one internal flange element (52) with a radially inner end (62) that is integrally molded with said stem and that extends from said stem and at a radially outward and forward incline from a position along said stem that is rearward of said front end (44) of said main flange and that has a radially outward end (64) that bears against an inside surface (18) of said main flange.

3. The earplug described in claim 2 including:
a backup flange (54) that has a backup flange front end (62) that is integral with said stem, said backup flange extending at a rearward and radially outward incline from said backup flange front end and pressing radially outward against said internal flange element.

4. The earplug described in claim 1 wherein:
said earplug has a front end part where the outside surface of said flange is of bullet shape and rearward of said front end part said inward and outward surfaces (22, 30) of said flange are primarily parallel, with the flange thickness (T) gradually decreasing toward the rear (R) of the flange along said length (L) that is at least 80% of the main flange maximum outside diameter.

5. The earplug described in claim 1 wherein:
said main flange has a front end (44) that merges at a joint location (24) with said front end part (20);
said main flange extends primarily rearward from said main flange front end (44) to a rear (48) end of said main flange with said main flange having a length (L) parallel to said axis along both said inner and outer flange surfaces, that is at least 75% of the length (G) of said earplug from a front end of said earplug to the rear end of said main flange, and with said main flange inside and outside surfaces each being of progressively greater diameter at more rearward locations along said main flange.

6. The earplug described in claim 1 wherein:
said main flange rear end has a diameter (D) of 0.35 inch to 0.60 inch, said main flange has a front end (44) that merges with said stem by means of said integral molding, and said main flange has a length (L) of at least 0.45 inch, with said main flange inner surface (22) extending at a rearward outward incline (C) away from said axis along the entire distance between said flange front end and a rear end (48) of said flange.

7. The earplug described in claim 1 wherein:
said earplug has a single flange on its outside that is formed by said main flange and that extends at said rearward incline (C) of between 5° and 25° to said axis along a majority of the main flange length, for engaging and blocking the ear canal, and said earplug is devoid of a forward portion lying forward of said flange that is of sufficient diameter to block the ear canal.

8. An earplug of elastomeric material having an axis (16), said earplug having an earplug front end (46), a stem (12) extending rearward along said axis from said earplug front end, and a flange (14) molded integrally with said stem and said earplug front end, said flange having a flange front end (44) merging with said stem and said flange extending primarily at a rearward and radially outward incline with respect to said axis from said flange front end to a free flange rear end (48), and said flange having inner and outer flange surfaces (22, 30) that result in a small thickness (T) between said flange surfaces to allow conforming of the flange rear portion to irregularities in the ear canal walls, wherein:
said earplug has a predetermined portion that extends along a length G between said earplug front end (46) and said flange rear end (48), with said flange inner and outer flange surfaces each extending at rearward and radially outward incline angles (C) of at least 5° but no more than 25° to said axis, along a length (L) parallel to said axis, that is at least 75% of said length (G) of said predetermined portion.

9. The earplug described in claim 8 wherein:
said thickness (T) between said flange inner and outer surfaces decreases toward the rear (R) of the flange.

* * * * *